United States Patent
Botzer et al.

(10) Patent No.: US 11,109,936 B2
(45) Date of Patent: *Sep. 7, 2021

(54) CATHETER STABILITY INDICATION

(71) Applicant: BIOSENSE WEBSTER (ISRAEL) LTD., Yokneam (IL)

(72) Inventors: Lior Botzer, Timrat (IL); Eitan Peri, Givat Ada (IL); Abraham Berger, Givatayim (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 219 days.

This patent is subject to a terminal disclaimer.

(21) Appl. No.: 16/449,698

(22) Filed: Jun. 24, 2019

(65) Prior Publication Data

US 2019/0307526 A1     Oct. 10, 2019

Related U.S. Application Data

(63) Continuation of application No. 14/860,021, filed on Sep. 21, 2015, now Pat. No. 10,327,859.

(51) Int. Cl.
*A61B 90/10* (2016.01)
*A61B 90/00* (2016.01)
*A61B 18/14* (2006.01)
*A61B 18/00* (2006.01)
*A61B 17/00* (2006.01)

(52) U.S. Cl.
CPC .......... *A61B 90/06* (2016.02); *A61B 18/1492* (2013.01); *A61B 90/10* (2016.02); *A61B 2017/00199* (2013.01); *A61B 2018/00029* (2013.01); *A61B 2018/00357* (2013.01); *A61B 2018/00577* (2013.01); *A61B 2018/00797* (2013.01); *A61B 2018/00815* (2013.01);
(Continued)

(58) Field of Classification Search
CPC ..... A61B 90/06; A61B 90/10; A61B 18/1492; A61B 2080/065; A61B 2018/00815; A61B 2018/00029; A61B 2018/00577
See application file for complete search history.

(56) References Cited

U.S. PATENT DOCUMENTS 6,129,669 A     10/2000 Panescu
6,226,542 B1     5/2001 Reisfeld
(Continued)

FOREIGN PATENT DOCUMENTS

CN     102106752 A     6/2011
CN     104665926 A     6/2015
(Continued)

OTHER PUBLICATIONS

U.S. Appl. No. 13/589,347, filed Aug. 20, 2012.
U.S. Appl. No. 14/551,299, filed Nov. 24, 2014.

*Primary Examiner* — Michael F Peffley
*Assistant Examiner* — Bo Ouyang

(57) ABSTRACT

A probe having a temperature sensor on its distal portion is introduced into a fluid-filled body cavity of a subject, and an irrigating fluid passed through the probe. The temperature of the irrigating fluid exiting the probe differs from the temperature of the body cavity. Temperature readings of the irrigating fluid exiting the probe are recorded. A determination is made from the temperature readings that predetermined contact criteria between the probe and the interior wall of the body cavity are satisfied.

14 Claims, 11 Drawing Sheets

(52) U.S. Cl.
CPC .............. *A61B 2018/00821* (2013.01); *A61B 2090/065* (2016.02); *A61B 2218/002* (2013.01)

(56) References Cited

U.S. PATENT DOCUMENTS

| | | | |
|---|---|---|---|
| 6,241,724 B1 | 6/2001 | Fleischman | |
| 6,301,496 B1 | 10/2001 | Reisfeld | |
| 6,695,808 B2 | 2/2004 | Tom | |
| 6,709,432 B2 | 3/2004 | Ferek Patric | |
| 6,814,733 B2 | 11/2004 | Schwartz | |
| 6,892,091 B1 | 5/2005 | Ben Haim | |
| 6,915,149 B2 | 7/2005 | Ben Haim | |
| 6,997,924 B2 | 2/2006 | Schwartz | |
| 7,156,816 B2 | 1/2007 | Schwartz | |
| 7,536,218 B2 | 5/2009 | Govari | |
| 7,756,576 B2 | 7/2010 | Levin | |
| 8,456,182 B2* | 6/2013 | Bar-Tal | A61B 5/053 324/713 |
| 8,603,084 B2 | 12/2013 | Fish | |
| 2006/0259023 A1* | 11/2006 | Abboud | A61B 18/02 606/21 |
| 2007/0100332 A1 | 5/2007 | Paul | |
| 2008/0275465 A1* | 11/2008 | Paul | A61B 18/1206 606/129 |
| 2008/0288038 A1 | 11/2008 | Paul | |
| 2011/0224664 A1* | 9/2011 | Bar-Tal | A61B 18/1492 606/33 |
| 2012/0165809 A1* | 6/2012 | Christian | A61B 18/1492 606/41 |
| 2013/0123770 A1* | 5/2013 | Smith | A61B 18/082 606/28 |
| 2013/0172875 A1 | 7/2013 | Govari | |
| 2014/0051959 A1 | 2/2014 | Gliner | |
| 2014/0171821 A1 | 6/2014 | Govari | |
| 2015/0018813 A1* | 1/2015 | Gliner | A61B 18/1233 606/33 |

FOREIGN PATENT DOCUMENTS

| | | |
|---|---|---|
| JP | 2012239915 A | 12/2012 |
| JP | 2015107378 A | 6/2015 |
| WO | WO2004103230 A1 | 12/2004 |

\* cited by examiner

CATHETER STABILITY INDICATION

CROSS REFERENCE TO RELATED APPLICATIONS

This application is a continuation application of U.S. patent application Ser. No. 14/860,021, filed Sep. 21, 2015, the entire contents of which are hereby incorporated by reference.

BACKGROUND OF THE INVENTION

1. Field of the Invention

This invention relates to tissue ablation systems. More particularly, this invention relates to monitoring of contact between an invasive probe and tissue within the body.

2. Description of the Related Art

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating such arrhythmias include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

Verification of physical electrode contact and contact stability with the target tissue is important for controlling the delivery of ablation energy. Attempts in the art to verify electrode contact with the tissue have been extensive, and various techniques have been suggested. For example, U.S. Pat. No. 6,695,808 describes apparatus for treating a selected patient tissue or organ region. A probe has a contact surface that may be urged against the region, thereby creating contact pressure. A pressure transducer measures the contact pressure. This arrangement is said to meet the needs of procedures in which a medical instrument must be placed in firm but not excessive contact with an anatomical surface, by providing information to the user of the instrument that is indicative of the existence and magnitude of the contact force.

As another example, U.S. Pat. No. 6,241,724 describes methods for creating lesions in body tissue using segmented electrode assemblies. In one embodiment, an electrode assembly on a catheter carries pressure transducers, which sense contact with tissue and convey signals to a pressure contact module. The module identifies the electrode elements that are associated with the pressure transducer signals and directs an energy generator to convey radiofrequency (RF) energy to these elements, and not to other elements that are in contact only with blood.

A further example is presented in U.S. Pat. No. 6,915,149. This patent describes a method for mapping a heart using a catheter having a tip electrode for measuring local electrical activity. In order to avoid artifacts that may arise from poor tip contact with the tissue, the contact pressure between the tip and the tissue is measured using a pressure sensor to ensure stable contact.

U.S. Patent Application Publication 2007/0100332 describes systems and methods for assessing electrode-tissue contact for tissue ablation. An electromechanical sensor within the catheter shaft generates electrical signals corresponding to the amount of movement of the electrode within a distal portion of the catheter shaft. An output device receives the electrical signals for assessing a level of contact between the electrode and a tissue.

Impedance-based methods for assessing catheter-tissue contact that are known in the art typically rely on measurement of the magnitude of the impedance between an electrode on the catheter and a body-surface electrode. When the magnitude is below some threshold, the electrode is considered to be in contact with the tissue. This sort of binary contact is sensitive to changes in the impedance between the body-surface electrode and the skin.

U.S. Patent Application Publication Nos. 2008/0288038 and 2008/0275465, both by Sauarav et al., which are herein incorporated by reference, describe an electrode catheter system, which may comprise an electrode adapted to apply electric energy. A measurement circuit adapted to measure impedance may be implemented between the electrode and ground as the electrode approaches a target tissue. A processor or processing units may be implemented to determine a contact condition for the target tissue based at least in part on reactance of the impedance measured by the measurement circuit. In another embodiment, the contact condition may be based on the phase angle of the impedance.

SUMMARY OF THE INVENTION

Newer cardiac catheters include temperature-sensing elements that provide information on the temperature distributions of the catheter tip and the relative orientation of the catheter tissue interface. This information enables an estimation of the size of an ablation lesion. The inventors have found that such temperature information in conjunction with strategically applied cooling irrigation of a target ablation site can be exploited prior to delivery of ablation energy to establish whether the catheter-tissue interface is stable or not.

A known difficulty in the use of ablation energy, e.g., radiofrequency energy for cardiac tissue ablation is controlling local heating of tissue. There are tradeoffs between the desire to create a sufficiently large lesion to effectively ablate an abnormal tissue focus, or block an aberrant conduction pattern, and the undesirable effects of excessive local heating. If the radiofrequency device creates too small a lesion, then the medical procedure could be less effective, or could require too much time. On the other hand, if tissues are heated excessively then there could be local charring effects, coagulum, and or explosive steam pops due to overheating. Such overheated areas can develop high impedance, and may form a functional barrier to the passage of heat. The use of slower heating provides better control of the ablation, but unduly prolongs the procedure. Normally, irrigation precedes the ablation process. Irrigation lowers the temperature at the interface, since irrigation fluid is colder than the blood and the tissue.

The transient temperature pattern and its steady state differ when the catheter is stable against the tissue and when it is not, When the catheter is stable only limited regions are cooled, whereas an unstable catheter-tissue interface is characterized by a relatively more dispersed distribution of irrigation fluid. The temperature phenomena described in further detail herein are observable so long as the irrigation fluid is colder than the blood/tissue temperature. Within this constraint, the temperature of the irrigation fluid and its flow rate mainly affect the magnitude of the differential signals, and their signal-to-noise ratio.

There is provided according to embodiments of the invention a method, which is carried out by introducing a probe having a temperature sensor on its distal portion into a fluid-filled body cavity of a subject, and passing an irrigating fluid through the probe, wherein the irrigating fluid exits the probe at its distal portion and wherein the temperature of the irrigating fluid is different from the temperature of the body cavity. The method is further carried out while passing the irrigating fluid by recording temperature readings of the temperature sensor, and making a determination from the temperature readings that predetermined contact criteria between the probe and the interior wall of the body cavity are satisfied, and thereafter alerting an operator that the contact criteria are satisfied.

According to a further aspect of the method, passing an irrigating fluid is performed multiple times at different flow rates.

Yet another aspect of the method includes deriving a blood temperature and an irrigation fluid temperature from the temperature readings at respective flow rates.

According to an aspect of the method, the contact criteria comprise criteria for stable contact between the probe and the interior wall of the body cavity.

According to yet another aspect of the method, the contact criteria comprise criteria for unstable contact between the probe and the interior wall of the body cavity.

According to still another aspect of the method, the contact criteria comprise criteria for an absence of contact between the probe and the interior wall of the body cavity.

According to one aspect of the method, the probe has a plurality of temperature sensors, and recording temperature readings is performed concurrently with the temperature sensors.

An additional aspect of the method includes thermally insulating the temperature sensors from the irrigating fluid passing through the probe.

According to a further aspect of the method, the temperature sensors are disposed on an external surface of the probe.

According to yet another aspect of the method, the temperature sensors are disposed internally in the probe.

According to another aspect of the method an ablation electrode on the probe is activated while recording temperature readings.

In yet another aspect of the method recording temperature readings includes recording a first temperature reading and thereafter recording a second temperature reading. The contact criteria are satisfied when the second temperature reading is lower than the first temperature reading, the method includes reporting contact between the probe with the interior wall.

According to still another aspect of the method, the second temperature reading is at least 1° C. lower than the first temperature reading.

According to a further aspect of the method, the second temperature reading is at least 4° C. lower than the first temperature reading.

An additional aspect of the method the second temperature reading further comprise transient elevations of between 1 to 4° C. that are between 0.3 to 5 seconds in duration, the method includes reporting an intermittent contact between the probe and the interior wall.

Another aspect of the method includes filtering the temperature readings to remove effects of heart rate variations and respiratory fluctuations.

There is further provided according to embodiments of the invention an apparatus, including a probe adapted for insertion into a fluid-filled body cavity of a subject, the probe includes a temperature sensor on a distal portion of the probe, The apparatus includes a pump for passing an irrigating fluid through the probe, wherein the irrigating fluid exits the probe at the distal portion and wherein a temperature of the irrigating fluid is different from a temperature of the body cavity, and a processor operative for recording temperature readings of the temperature sensor while the pump is passing the irrigating fluid, making a determination from the temperature readings that predetermined contact criteria between the probe and the interior wall of the body cavity are satisfied, and thereafter alerting an operator that the contact criteria are satisfied.

An ablation electrode is provided on the distal portion of the probe, which may be activated while recording temperature readings.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a diskette, hard drive, electronic media or CD-ROM. The code may be distributed on such media, or may be distributed to users from the memory or storage of one computer system over a network of some type to storage devices on other computer systems for use by users of such other systems.

System Overview.

Figure 1:
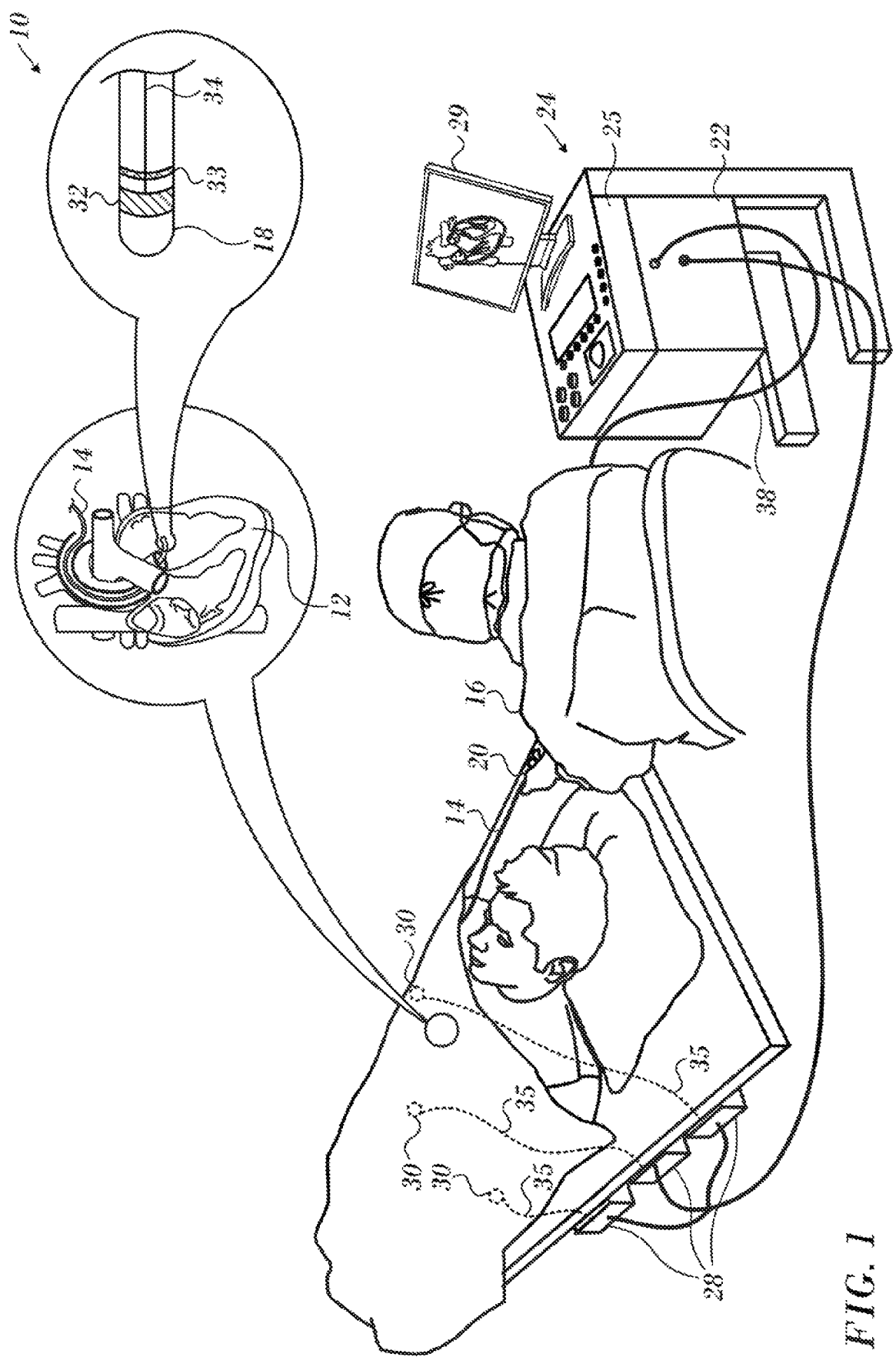
FIG. 1 is a pictorial illustration of a system for performing diagnostic and therapeutic procedures in accordance with an embodiment of the invention.

Turning now to the drawings, reference is initially made to FIG. 1, which is a pictorial illustration of a system 10 for evaluating electrical activity and performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to em-body the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system for measuring location and orientation coordinates of the catheter 14. The processor 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32. The sensors can vary in position. For example, the sensors may be external or internal to the catheter a 14. In any case the sensors are thermally insulated from irrigating fluid passing through the catheter using any conventional insulating material.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning sub-system is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by sensors such as electrical, temperature and contact force sensors, and a plurality of location sensing electrodes (not shown) located distally in the catheter 14. The digitized signals are received and used by the console 24 and the positioning system to compute the position and orientation of the catheter 14, and to analyze the electrical signals from the electrodes.

In order to generate electroanatomic maps, the processor 22 typically comprises an electroanatomic map generator, an image registration program, an image or data analysis program and a graphical user interface configured to present graphical information on the monitor 29.

Typically, the system 10 includes other elements, which are not shown in the figures for the sake of simplicity. For example, the system 10 may include an electrocardiogram (ECG) monitor, coupled to receive signals from one or more body surface electrodes, in order to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12.

Conventional pumps and lines for circulating liquids through the catheter 14 for cooling the ablation site are provided. The system 10 may receive image data from an external imaging modality, such as an MRI unit or the like and includes image processors that can be incorporated in or invoked by the processor 22 for generating and displaying images.

Figure 2:
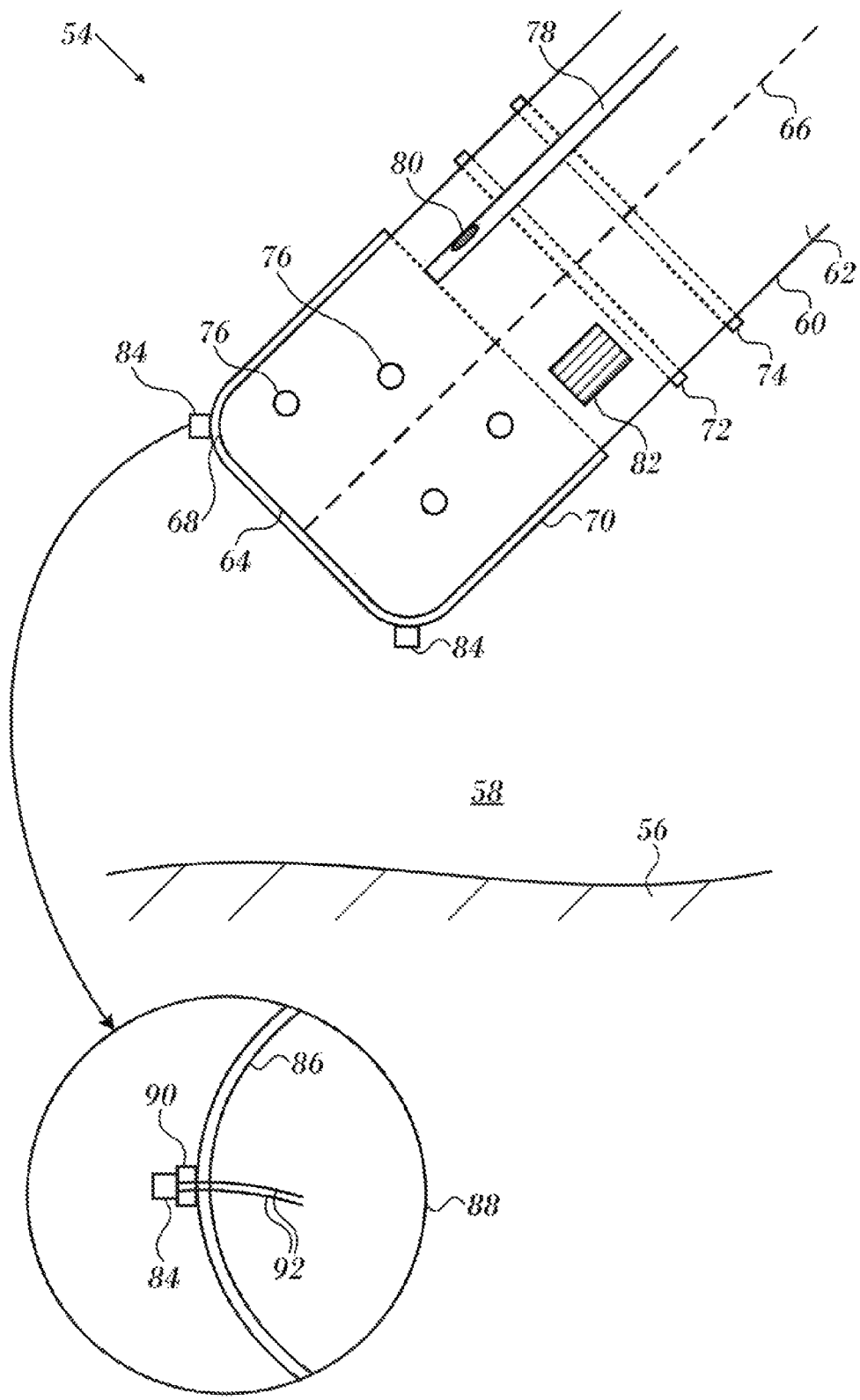
FIG. 2 is a sectional view along the length of the distal segment of a cardiac catheter, in accordance with an embodiment of the invention.

Reference is now made to FIG. 2, which is a sectional view along the length of distal segment 54 of a cardiac catheter in accordance with an embodiment of the invention. The distal segment 54 is in proximity to tissue 56, and is assumed to be immersed in fluid 58, so that tissue 56 has a surface 29 contacting the fluid. Fluid 58 typically comprises a mixture of blood and saline solution. By way of example, distal segment 54 is assumed herein to be formed from an insulating substrate 60 in the shape of a cylinder 62 closed by a generally flat surface 64 at one end. Cylinder 62 has an axis of symmetry 66. As shown in FIG. 2, a curved section 68 joins flat surface 64 and cylinder 62. A typical diameter of cylinder 62 is 2.5 mm, and a typical radius of the curved section 68 is 0.5 mm.

Distal segment 54 comprises three electrodes 70, 72, 74, the electrodes being insulated from each other. The electrodes 70, 72, 74 typically comprise thin metal layers formed over insulating substrate 60. Typically, the distal tip has other electrodes, insulated from the electrodes 70, 72, 74, which for simplicity are not shown in the diagram. Tip electrode 70 has the shape of a cup with a flat base, and is herein also referred to as the cup electrode. Cup electrode 70 typically has a thick-ness in a range from approximately 0.1 mm to approximately 0.2 30 mm. Second and third electrodes 70, 72, are usually in the form of rings, and are also known as ring electrodes.

Electrodes 70, 72, 74 are connected to a controller in console 24 (FIG. 1) by wires (not shown). At least one of the electrodes is used to ablate tissue 56. Typically, during ablation, heat is generated in the ablating electrode and in the surrounding region. In order to dissipate the heat, small irrigation apertures 76 in the cup electrode. The apertures 76 typically have diameters in an approximate range 0.1-0.2 mm. An irrigation tube 78 supplies saline solution to the apertures 76, and the rate of flow of the saline solution through the apertures 76 (causing fluid 58 to be a mixture of blood and saline solution) is controlled by an irrigation module (not shown) in the console 24 (FIG. 1). The saline rate of flow is typically in the range of approximately 2-20 cc/minute, but may be higher or lower than this range.

A saline temperature sensor 80, typically a thermocouple, is located in tube 78, and provides a signal to circuitry in the console 24 (FIG. 1) module 56 enabling the console 24 to measure a temperature Ts of the saline solution input to apertures 76. While the saline solution may be provided at room ambient temperature, e.g., in a range of approximately 19-25° C., the solution may be heated slightly during its flow through the catheter, so that the final irrigation temperature may be slightly higher.

Typically, one or more location sensing devices 82 are incorporated in the distal tip. Devices 82 are configured to provide signals to the processor 22 (FIG. 1) enabling the system to ascertain the position and/or orientation of distal segment 54, In one embodiment distal segment 54 comprises one or more generally similar temperature sensors 84 (by way of example, two are shown in the diagram) which are fixedly connected, by an insulator, to the outer surface of cup electrode 70, so as to protrude from the surface. Sensors 84 have a typical diameter of approximately 0.3 mm and a length of approximately 1.5 mm. In one embodiment sensors 84 are thermistors NTC Type AB6, produced by General Electric Company of Schenectady, N.Y. In an alternative embodiment, sensors 84 comprise "F" type thermistors produced by Semitec USA Corporation of Torrance, California. By way of example, the following description assumes there are three sensors 84 symmetrically distributed with respect to axis 51, and located on a curved section 86 of the cup electrode. Curved section 86 of the cup electrode overlays curved section 68 of the distal tip. Curved section 86 is in the shape of a partial toroid, typically a partial torus having a tube radius of approximately 0.5 mm.

A magnified section 88 of FIG. 2 illustrates one of sensors 84 in more detail. As shown in section 88, an insulator 90 separates sensors 84 from curved section 86 of the cup electrode 70. Insulator 90 is selected to provide good thermal and electrical insulation, and in some embodiments insulator 90 may comprise an adhesive that bonds sensors 84 to curved section 86. Wires 92 90 connect sensors 84 to the console 24 (FIG. 1).

By having sensors 84 protrude from the outer surface of cup electrode 70, the sensors 84 are able to intimately contact tissue 56. The processor 22 (FIG. 1) is thus able to use signals from the sensors 84 to provide direct temperature measurements of the tissue 56 In one embodiment the sensors 84 protrude from the outer surface of the electrode 70 by no more than 0.7 mm, and typically by approximately 0.5 mm.

Figure 3:
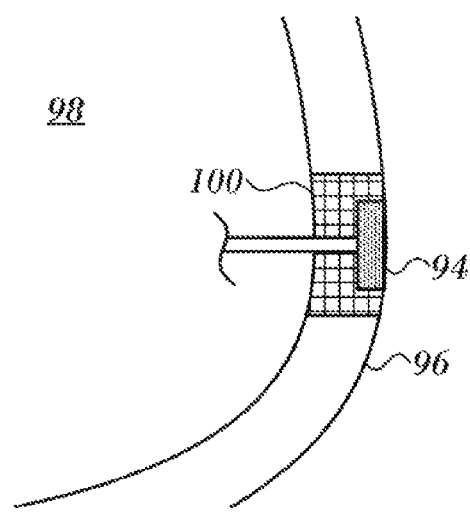
FIG. 3 is a detailed view of a portion of the distal segment of a cardiac catheter in accordance with an alternate embodiment of the invention.

Reference is now made to FIG. 3, which is a detailed view of a portion of the distal segment of a cardiac catheter in accordance with an alternate embodiment of the invention. In this embodiment the sensors do not protrude above the outer surface of the cap electrode or the outer surface of the probe. In the representative example of FIG. 3 sensor 94 is flush with outer surface 96 and is insulated from fluid passing through lumen 98 by an insulating material 100. An advantage of this embodiment is a reduction in the likelihood of thrombus formation on the surface of the sensor 94.

Figure 4:
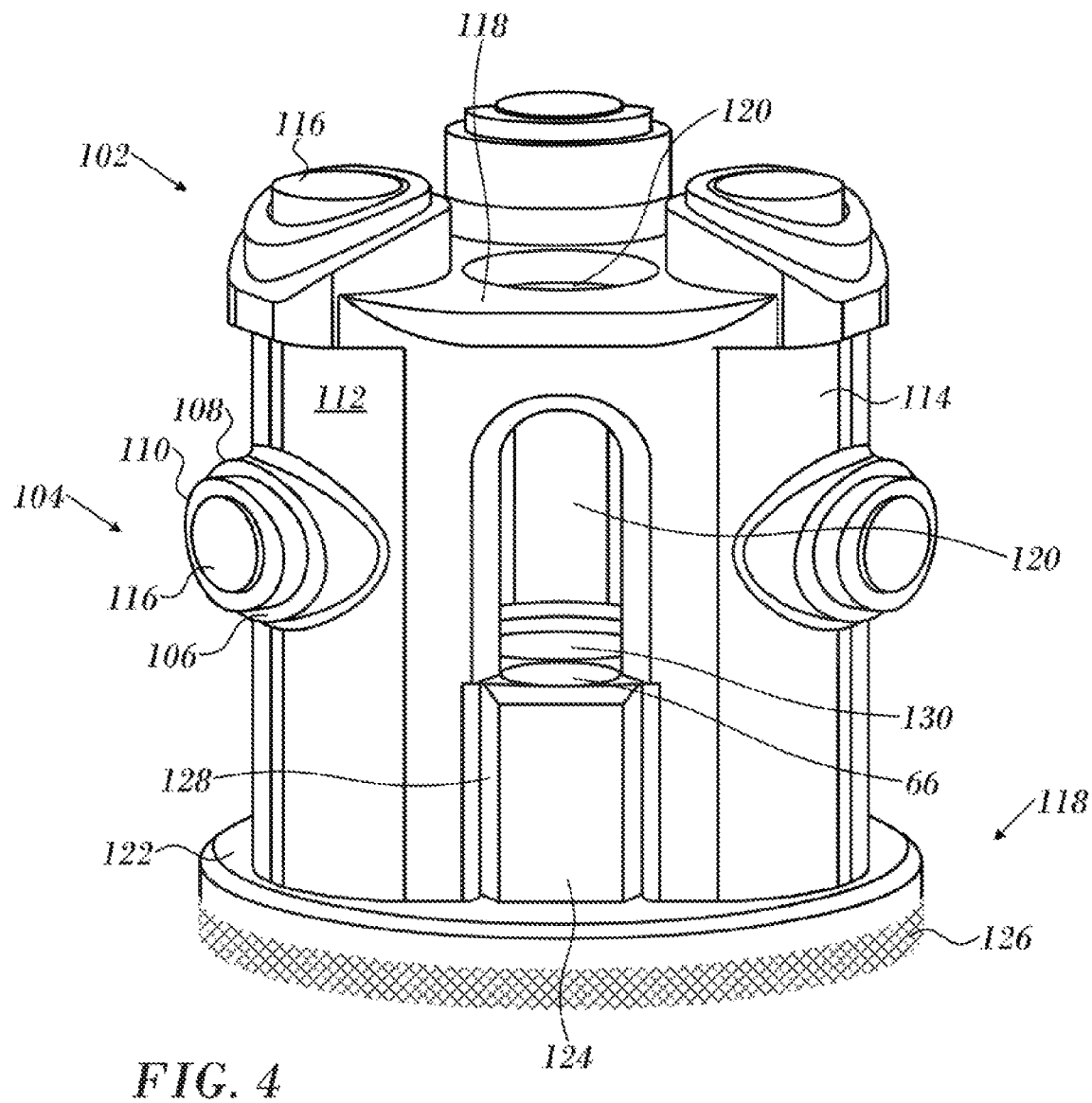
FIG. 4 is an isometric view of an insert for a catheter in accordance with an embodiment of the invention.

Reference is now made to FIG. 4, which is an isometric view of an insert 102 for a catheter in accordance with an embodiment of the invention. The insert 102 is adapted to be capped by cap electrode in the catheter similar to the electrode 70 (FIG. 2), The cap electrode is omitted for clarity.

As can be seen, protrusions 104 include annular shoulders 106 configured to engage the inner surface of the ablation electrode. Shoulders 106 may have a surface that is complimentary to the internal surface of the cap electrode as appropriate. The width of shoulders 106 may be defined by the difference between the diameter of a base portion 108 and the diameter of inner portion 110. The diameter of inner portion 110 is sized to mate with sensor orifices (not shown, The protrusions 104 are configured to either extend outward from or are flush with the outer surface of the cap electrode. Similarly, annular shoulders 106 extend radially outward from the surface of insert 102, such that the depth of base portion 108 establishes a minimum separation between the inner surface of the cap electrode and surface 112 on the body of insert 102.

In this embodiment, insert 102 includes three longitudinally extending arms 114, each having a hollow interior portion to allow routing of leads and wires to sensors 116. Arms 114 are connected at distal crown portion 118. Passageways 120 may be formed between arms 114 as well as by a central opening in crown portion 118. Depending on the intended use and the number of sensors being provided, the configuration of insert 102 may be adapted as desired, such as by featuring two or four arms, for example. In one aspect, each if the arms 114 may include at least two protrusions 104 to accommodate at least two sensors, such as one proximal and one distal.

Sensors 116 may be any combination of temperature sensors, e.g., thermistor, thermocouple, fluoroptic probe, and the like, or electrical sensors, e.g., micro-electrodes. Any temperature sensor junctions located at or near the end of protrusions 104 and may be potted with a thermally conductive adhesive. Any wires or leads associated with sensors 116 may be routed through arms 114 as appropriate. As will be appreciated, this configuration isolates sensors 116 from the cap electrode and the irrigation fluid. In one aspect, insert 102 serves to thermally insulate sensors 116. Accordingly, a more accurate measurement of tissue and environmental temperature may be obtained by reducing biasing from the cap electrode or the circulating irrigation fluid. In another aspect, insert 102 also serves to electrically insulate sensors 116 to allow more accurate measurement. Similarly, any wires and/or leads are also thermally and electrically insulated, as well as being sealed against corrosion from the irrigation fluid. In one aspect, each of the sensors 116 that are positioned by the protrusions 104 may be configured to sense a plurality of measurements. For example, one or more sensors 116 may function both as a micro-thermistor and a micro-electrode. According to one embodiment, thermistor wires as well as an electrode lead wire may be connected to a shell cap electrode of each of the sensors 116. Each wire may be isolated from each other by any suitable technique, such as by employing a suitable electrically nonconductive and non-thermally insulative material to fill the interior of arms 114 after placement of sensors 116.

Insert 102 is stabilized within the cap electrode by portion 118, which includes a disc-shaped base 122 and a distally projecting key 124. Base 122 may have a diameter corresponding to the inner diameter of the cap electrode and may be secured in any suitable manner, such as by welding 126. Key 124 is configured to fit within recess 128 of insert 102, formed by the proximal portions of arms 114, to stabilize insert 102 against axial rotation and possible displacement of sensors 116. Portion 118 may provide a fluid-tight seal with cap electrode while routing leads and wires associated with the cap electrode, sensors 116 and irrigation fluid from lumens extending through the catheter body. For example, central conduit 130 may be in communication with the lumen of the catheter to conduct irrigation fluid to passageways 120, for circulation within the interior of the cap electrode and eventual exit through apertures, e.g., apertures 76 (FIG. 2).

Catheters of the kind described with reference to FIG. 2 and FIG. 4 are described in further detail in commonly assigned U.S. Patent Application Publication Nos. 2014/0171821 by Govari et al., 2011/10224664 to Bar-Tal et al., and copending U.S. application Ser. No. 14/551,229, entitled Irrigated Ablation Catheter with Multiple Sensors, which are herein incorporated by reference.

Operation.

Figure 5:
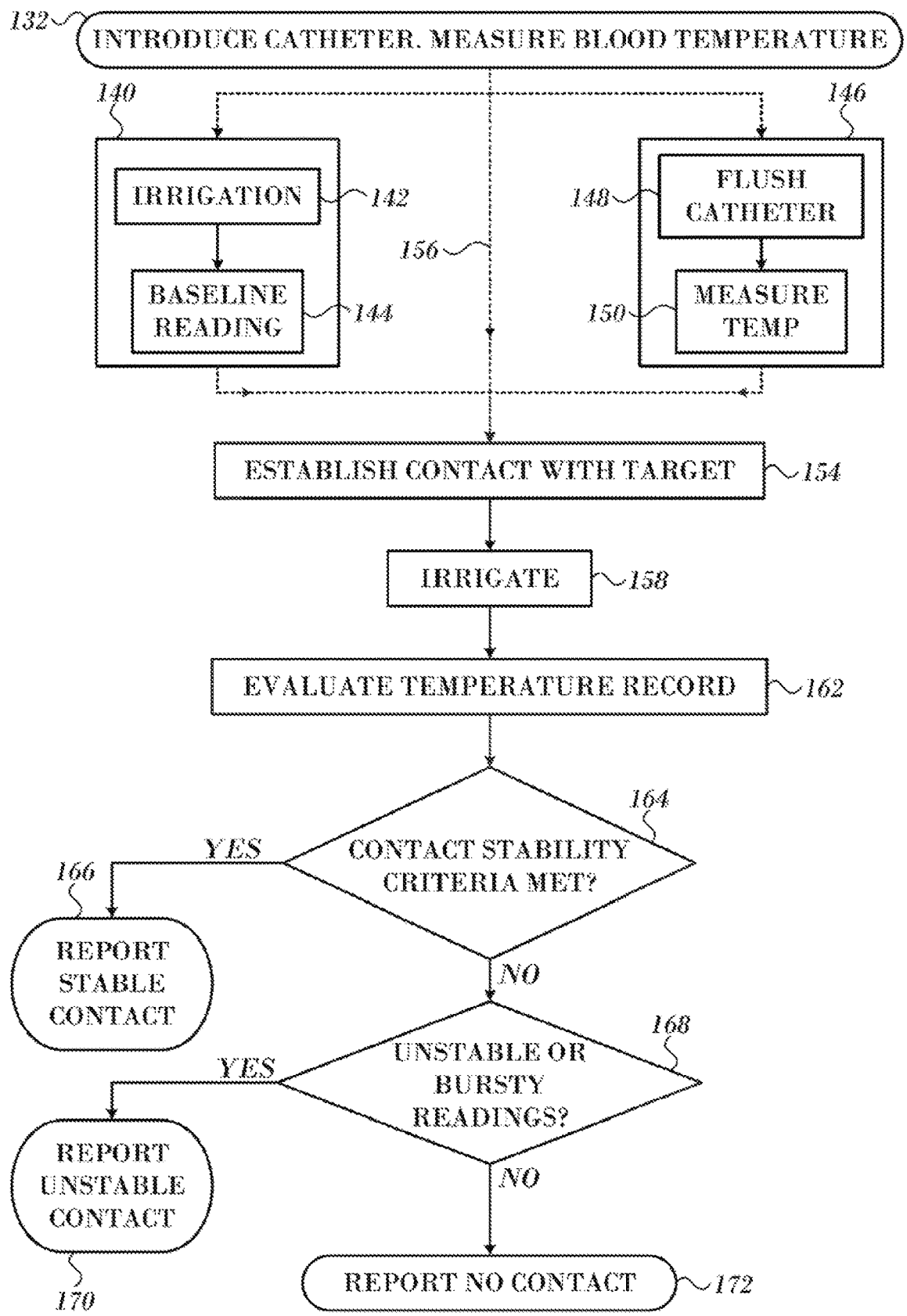
FIG. 5 is a flow-chart of a method of determining catheter-tissue interface stability, in accordance with an embodiment of the invention.

Reference is now made to FIG. 5, which is a flow-chart of a method of determining catheter-tissue interface stability, in accordance with an embodiment of the invention. In the drawings herein, process steps are shown in a particular linear sequence for clarity of presentation. However, it will be evident that many of them can be performed in parallel, asynchronously, with feedback loops, or in different orders. Those skilled in the art will also appreciate that a process could alternatively be represented as a number of interrelated states or events, e.g., in a state diagram. Moreover, not all illustrated process steps may be required to implement the process.

In the discussion below, the temperature of the irrigation fluid is lower than the temperature of the blood. An irrigation fluid at typical room temperature (25° C.) is suitable. However, the principles of the invention are applicable, mutatis mutandis, when the irrigation fluid is warmer than the blood.

At initial step 132, a cardiac catheter is introduced into the heart of a subject using well-known methods. At this stage, the catheter is still free in the cardiac chamber and out of contact with the wall of the heart. An optional calibration may be now performed. The goal of the calibration is to establish a temperature threshold for differentiating between two conditions: A) catheter in the blood pool; and B) catheter in contact (whether intermediate or not) with tissue. It is necessary to know the blood temperature, the irrigation fluid temperature. These can be assumed or measured. It is also necessary to know the flow rate of the irrigation fluid.

Figure 6:
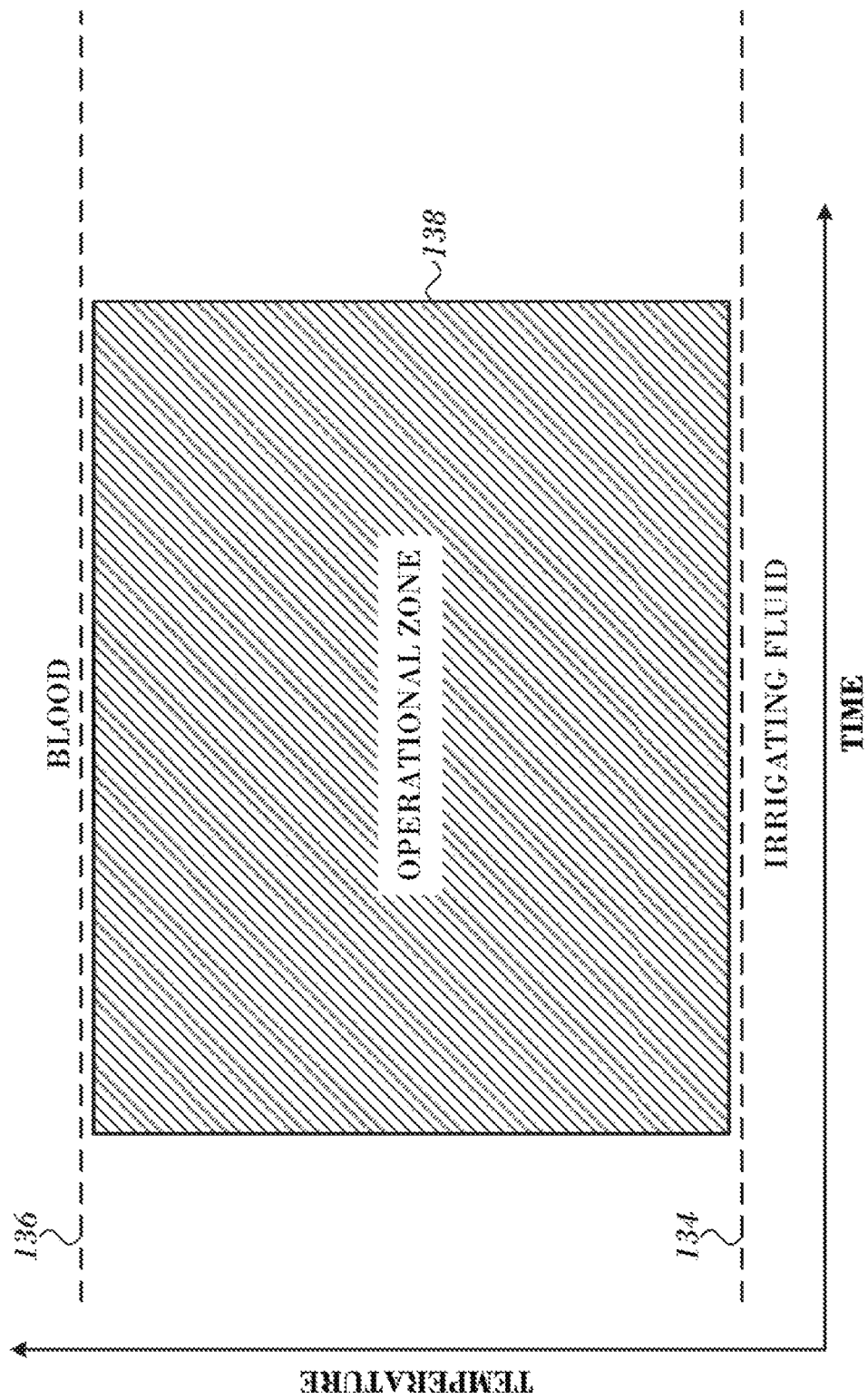
FIG. 6 is a diagram illustrating a calibration process in accordance with an embodiment of the invention.

Reference is now made to FIG. 6, which is a diagram illustrating the optional calibration process in accordance with an embodiment of the invention. Blood and irrigating fluid baseline temperatures are represented as broken lines 134, 136, respectively. Temperatures measured during the procedure described below with respect to FIG. 5 occur in an operational zone 138 that lies between the baseline temperatures. The blood temperature (line 134) may be determined during introduction of the catheter and prior to initiating irrigation using sensors in the catheter tip. Measurement of fluid temperature can be performed on the irrigation line or can be derived by providing irrigation fluid at known flow rates to the catheter, and measuring the observed temperatures. Irrigating fluid temperature (line 134) may be determined using either of the following two procedures. Both procedures establish baselines representing the temperature of the irrigating fluid.

Returning to FIG. 5, in a first calibration option shown in block 140, after introduction of the catheter irrigation is initiated at step 142. Then, at step 144 baseline temperature readings may be obtained directly from sensors in the irrigation fluid lines outside the patient's body. These readings are not influenced by blood temperature.

Additionally or alternatively, in step 142, the irrigating fluid baseline readings may be taken concurrently with multiple temperature sensors in the catheter tip and should be continuous for a predetermined time interval, e.g., 2-5 sec, in order to establish a reliable pattern of variation. The predetermined time interval is not critical, and may be varied for particular applications. It may be desirable to flush the catheter with irrigation fluid after the time has elapsed. This alternative provides a baseline for a state in which the catheter is free in the cardiac chamber and being irrigated at a typical rate. The value obtained generally differs from that of the first alternative as there is some influence of ambient blood temperature.

In a second option, shown in block 146, an irrigation fluid baseline temperature is set by flushing the catheter at step 148 at different flow rates, typically with saline between 2 and 20 ml/sec and, at step 150, reading one or more temperature sensors during each flushing. Each flow of the flushings can be expressed in an equation that depends on the two knowns (the given flow rate and catheter build/design) and two unknowns blood and fluid temperature. By providing several flows the blood and fluid temperatures nay be obtained by solving a system of such equations. The geometry and other aspects of the catheter design are important as they affects the parameters. The parameters of the equations are therefore empirical, and catheter-specific. Significant catheter design issues include sensor locations (how well they sense the flow) and the design of the irrigation holes. Solution of the equations provides data on the fluid and the blood temperatures simultaneously. A precalibration process can be used for the equations.

During flushing, the temperature quickly drops from an ambient level to a threshold value (line 134; FIG. 6), which is close to the temperature of the fluid used for flushing. Additionally or alternatively, one or more additional sensors (not shown) may be located along the catheter in order to monitor the saline temperature as it enters the catheter and to measure the temperature of the blood. Using the information provided by the additional sensors, and solving the above-noted equations, it is possible to estimate the expected temperature readings of temperature sensors 152 in the blood pool prior to determining tissue contact with the catheter.

In either of the procedures described in blocks 140, 146, once irrigation begins, the temperature readings from the catheter tip drop from the blood temperature baseline (line 136; FIG. 6). For example, once a temperature reading below a predetermined threshold value, e.g., 32° C., is observed, it may be concluded that irrigation has begun. After completing step 144, or step 150 control proceeds to step 154.

In some embodiments the procedures of blocks 140, 146 are omitted, as the transitions described below, e.g., in the discussion of FIG. 8, can be established without reference to baselines or threshold readings. The baseline values may be assumed, e.g., based on experience or known information. It would be known from other modalities if the patient were febrile or hypothermic. In this case, control proceeds from initial step 132 directly to step 154 as shown by line 156.

Next, at step 154 contact is established between the tissue and the ablation electrode, which is typically located at the distal tip when the new position is attained of the catheter. This may be accomplished by any known method, e.g., any of the methods described above and the methods taught in U.S. Patent Application Publication No. 20130172875, entitled "Contact Assessment Based on Phase Measurement" and U.S. Patent Application Publication No. 20140051959 entitled "Machine Learning in Determining Catheter Electrode Contact", which are commonly assigned herewith and are herein incorporated by reference. Irrigation is begun at step 158. When contact has been established the temperature readings are intermediate between the blood and irrigation fluid baselines, (see FIG. 8; time 160).

Next, at step 162, while continuing irrigation, a record of temperature readings is obtained. Statistics, such as the mean temperature, variance, and the morphology of the temperature records are considered in step 162. If the catheter-tissue interface is unstable, the readings will be unstable, even bursty (as contact with a particular location occurs and is lost or as the contact point moves on the tissue. In the former case, the catheter tip is exposed to ambient blood. In the latter case, the catheter tip contacts uncooled tissue. In either case the temperature will rise or fall as contact is lost and reestablished in an unstable manner. Typically transient elevations of between 1 to 4° C. that are 0.3 to 5 sec in duration are seen when contact is intermittent or unstable. Such fluctuations may be due to respiration (5 sec per cycle, typically), heartbeat (0.3-1 sec/cycle) and pump pulsations within the range of 0.3 to 5 sec/cycle.

Next, at decision step 164, it is determined if criteria for stable contact based on the analysis of step 162 are satisfied. The criteria are empirically determined case-by-case, according to irrigation flow rate and the temperature of the irrigation fluid and the blood. If the determination at decision step 164 is affirmative, then control proceeds to final step 166. A stable catheter-tissue interface is reported, and ablation may begin.

If the determination at decision step 164 is negative then at decision step 168 it is determined if unstable or bursty readings temperature readings were obtained. If the determination at decision step 168 is affirmative, then control proceeds to final step 170. An unstable electrode-tissue interface is reported.

If the determination at decision step 168 is negative then control proceeds to final step 172. It is concluded that the catheter tip is free in the blood pool.

After performing one of final steps 166, 170, 172 the electrode is classified as being in stable contact, in intermittent contact or not in contact. The classification of each electrode can be based solely on the sensor data or derived from the behavior of several sensors. When multiple ablation electrodes are present, the sequence that follows step 142 may be performed separately for each electrode, and a respective contact status is reported for each of them.

Figure 7:
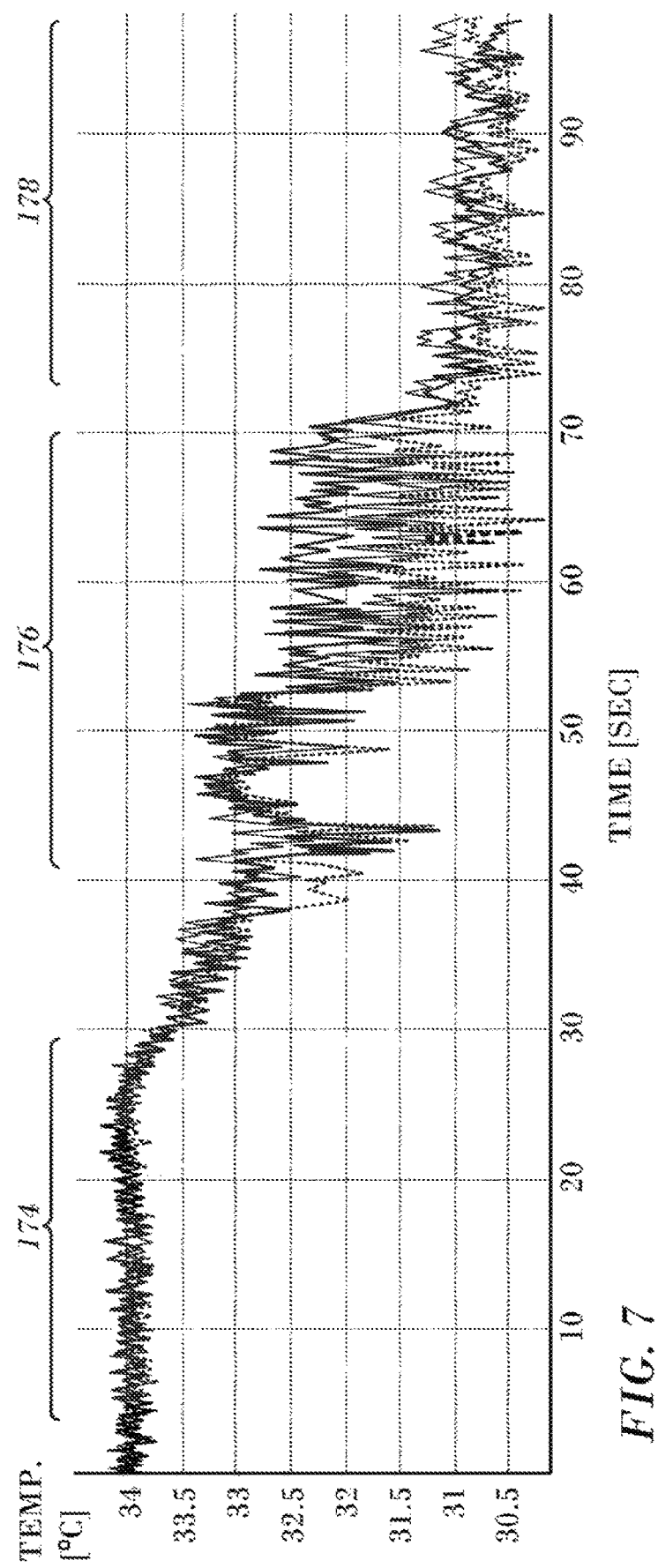
FIG. 7 is a chart indicating typical temperature tracings when the procedure of FIG. 5 is performed in accordance with an embodiment of the invention.

Reference is now made to FIG. 7, which is a chart indicating typical temperature tracings that are expected when a catheter is positioned in the heart, when the procedure of FIG. 5 is performed in accordance with an embodiment of the invention. During time interval 174, while the end of the catheter is free in the blood pool and out of contact with tissue, a relatively high temperature is recorded by the three temperature sensors, and there is little fluctuation. As noted above, the actual number of temperature sensors may vary in different embodiments. During time interval 176, intermittent contact with tissue exists. The temperature is lower, and there is a greater degree of fluctuation than in time interval 174. High frequency fluctuations are observed as the catheter alternates between contact and non-contact states. The alternations are an indication that the catheter is in close proximity to the tissue. Importantly, this demonstrates that there is not secure contact with the tissue In this event an alert may be generated for the operator, The fluctuation in this case correlates with mechanical movement of the cardiac wall as it moves against the catheter as the heart beats.) During time interval 178, the catheter is forcefully in contact with the tissue. The temperature is lowest and fluctuation intermediate among the time intervals 174, 176, 178. It is believed that the temperature is lowest because the irrigation fluid flowing from the catheter is cooling the tissue and the isolated sensor measures the tissue temperature. The transient temperature pattern and its steady state differ when the catheter is stable against the tissue and when it is not, When the catheter is stable only limited regions are cooled, whereas an unstable catheter-tissue interface is characterized by a relatively more dispersed distribution of irrigation fluid. Different measured temperatures are observed at the target site than when the catheter-tissue interface is stable and when it is not. The temperature phenomena described in further detail herein are observable so long as the irrigation fluid is colder than the blood/tissue temperature. Within this constraint, the temperature of the irrigation fluid and its flow rate mainly affect the magnitude of the differential signals, and their signal-to-noise ratio.

First Alternate Embodiment

In this embodiment, the signals obtained from the temperature sensors may be filtered using the signal processing circuitry of the system 10 (FIG. 1), e.g., by averaging the signal, or applying well-known filters directed to the frequencies of pump pulses, heart rate variations and respiratory fluctuations that would obscure other significant temperature fluctuations. In the first embodiment, high frequency fluctuations are intentionally not filtered, as their presence provides an excellent indication of intermittent contact with the tissue. Nevertheless, a filtering mode of operation is advantageous during periods of intermittent contact, as shown in the following example.

Example 1

This simulated example show the effect of dragging the electrode along the tissue. It consists of data obtained from a test system in which blood in a heart chamber was simulated by a water-filled aquarium (temperature 34° C.). Water at a temperature of 24° C. was pumped through a catheter, e.g., the catheters shown in FIG. 1, FIG. 2 having distal temperature sensors to simulate ablation site irrigation. Tissue contact was simulated by contacting the operator's hand to the distal portion of the catheter.

Figure 8:
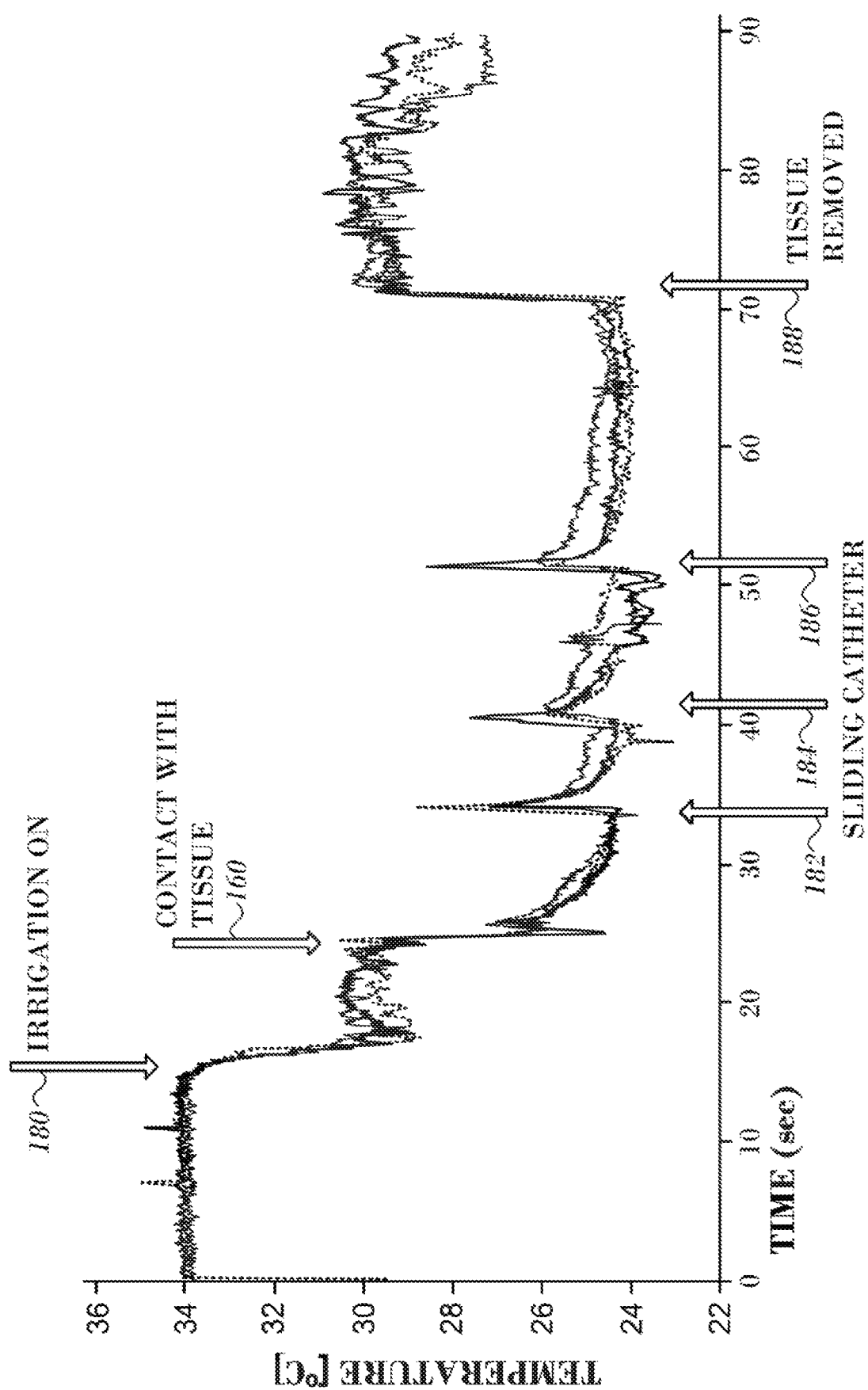
FIG. 8 is a chart that displays exemplary data in accordance with an embodiment of the invention.

Reference is now made to FIG. 8, which is a chart that displays data from this example in accordance with an embodiment of the invention. The data was recorded from three temperature sensors on the catheter. Temperature is plotted against time. Prior to time 180, the tip of the catheter was free in the aquarium, and the sensors recorded a temperature of 34° C., with very little variation. Irrigation was initiated at time 180. The temperature quickly dropped into a range of 25-30° C., with somewhat greater variation than prior to time 180. Heart rate and respiratory effects are necessarily omitted in this example.

At time 160 tissue contact was made with the catheter. Thereupon, the temperature dropped precipitously by about 4° C. to about 26° C., and thereafter declined more slowly, equilibrating at slightly above 24° C.

At time 182, an unstable catheter-tissue interface was simulated by sliding the catheter along the hand. Thus resulted in a transient elevation, i.e., a temperature spike of about 4° C. that was less than about 2 sec in duration, as the catheter contacted uncooled tissue. The temperature then gradually declined and approached the temperature of the irrigation fluid. This maneuver was repeated at times 184, 186. The spikes at times 182, 184, 186 reflect displacement of the catheter tip from a relatively stable position at one location. As the tip was repositioned by sliding it to another location, there was a period during which the tip was no longer in stable tissue contact. During this period the temperature rose transiently. Then, as a new relatively stable position was attained, the temperature dropped abruptly in the spiking pattern observed at times 182, 184, 186. It should be noted that without filtering the sensor signals, the spikes at times 182, 184, 186 would be obscured by fluctuations (e.g., fluctuations occurring during time interval 176; FIG. 7) caused by the above-noted artifacts.

Then the catheter was held in place until time 188. The temperature remained equilibrated near the temperature of the irrigation fluid, and met predefined stability criteria that can be established by known methods, e.g., excursions that are less than a threshold value for a certain time interval. Then at time 188, the catheter was abruptly removed from the tissue. This maneuver was associated with an immediate rise in temperature and a fluctuating tracing pattern.

Without being bound by any particular theory, the following discussion is offered as a possible explanation of the observed effects in order to facilitate understanding of the invention. When the catheter is in the blood pool it is exposed to the warm circulating blood (whether from the heart operation or from the combination of circulating irrigating flow and the blood) that maintain the catheter at a relative high temperature (typically around 34°-35°). The low temperature read by the sensors is an indication of the tissue being cooled by the catheter when it is in close proximity to the endocardial surface. The cooling occurs in a relatively small partially confined space. Therefore when the catheter slides on the tissue, it is exposed to higher temperatures of the blood pool and/or tissue that was not cooled by the fluid; hence the spike at time 182. When the catheter alternates between contact and blood pool it shows the spikes pattern of time interval 176 (FIG. 7).

Example 2

This example shows the relationships between contact, non-contact and flow rates. A pig was intubated and anesthetized, and catheterized using an open irrigation catheter having the arrangement shown in FIG. f4 with | six thermocouple sensors and a contact force sensor. The conditions that were tested were contact and non-contact, i.e., the tip of the catheter free in the blood pool. Contact status was verified by readings from the contact force sensor and by Carto mapping. In both contact and non-contact conditions three different irrigation flows were measured (2, 10, 25 ml/sec).

Figure 9:
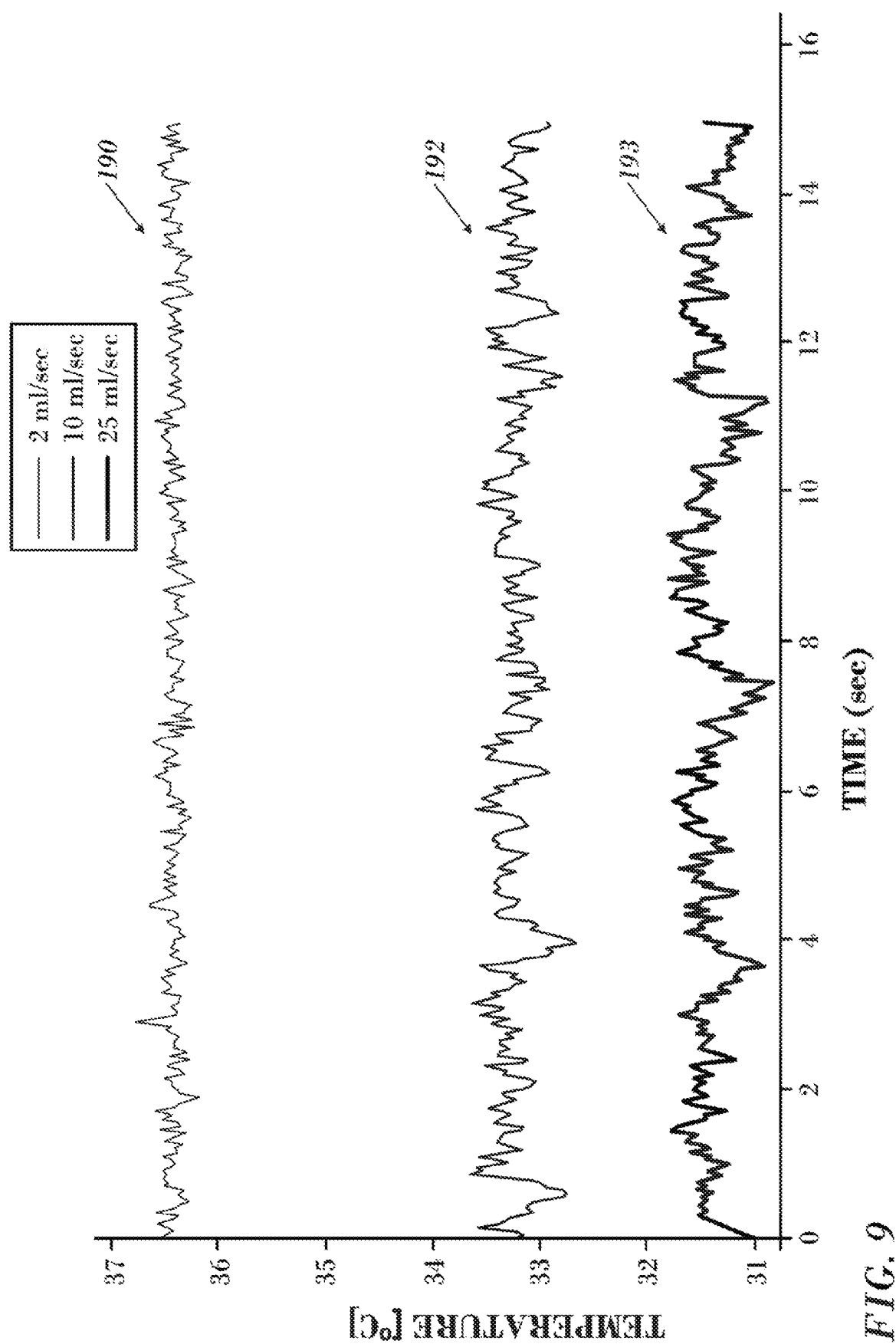
FIG. 9 is a graph showing average temperature measurement as a function of flow of irrigation fluid in accordance with an embodiment of the invention

Reference is now made to FIG. 9, which is a graph in accordance with an embodiment of the invention showing average temperature measurement from the 6 sensors, as a function of flow of irrigation fluid at room temperature when there is no contact between the catheter tip and the tissue. It is evident that the measured temperature drops as the flow rate increases. Tracings 190, 192, and 193 correspond to flow rates of 2, 10, and 25 ml/sec, respectively. At the 2 ml/sec rate the measured temperature does not differ significantly from the blood temperature. At 25 ml/sec a more substantial drop is seen, with an intermediate drop at 10 ml/sec.

Figure 10:
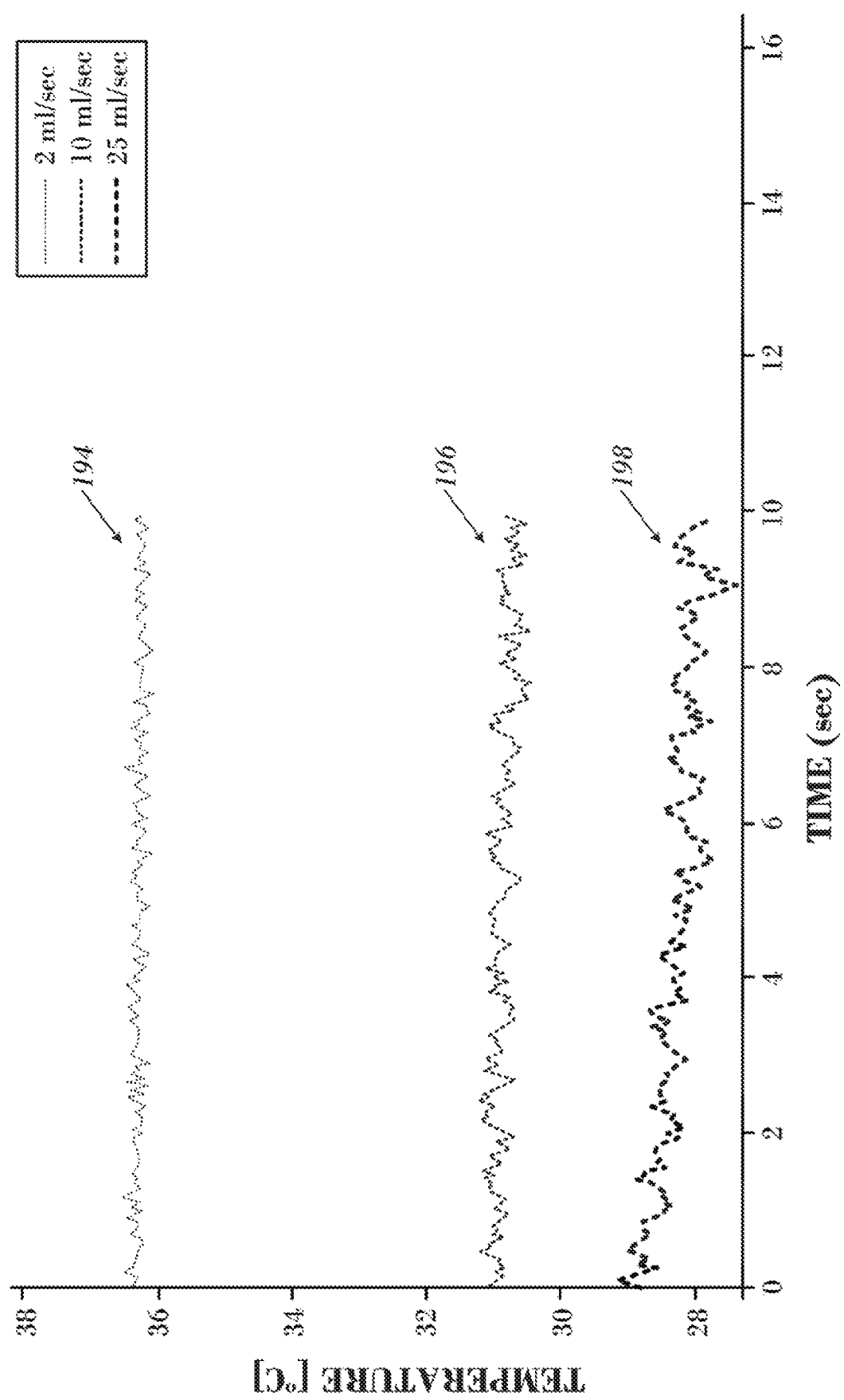
FIG. 10 is a graph showing average temperature measurement as a function of flow of irrigation fluid in accordance with an embodiment of the invention.

Reference is now made to FIG. 10, which is a graph in accordance with an embodiment of the invention showing average temperature measurement from the 6 sensors as a function of flow of irrigation fluid at room temperature when there is contact between the catheter tip and the tissue. The same conditions were used as in FIG. 9. Tracings 194, 196, 198 correspond to flow rates of 2, 10, and 25 ml/sec, respectively Contact was verified when a force exceeding 15 gr was ready by the contact force sensor. As in FIG. 9 a progression in the temperature drop is seen as the flow rate increases.

Figure 11:
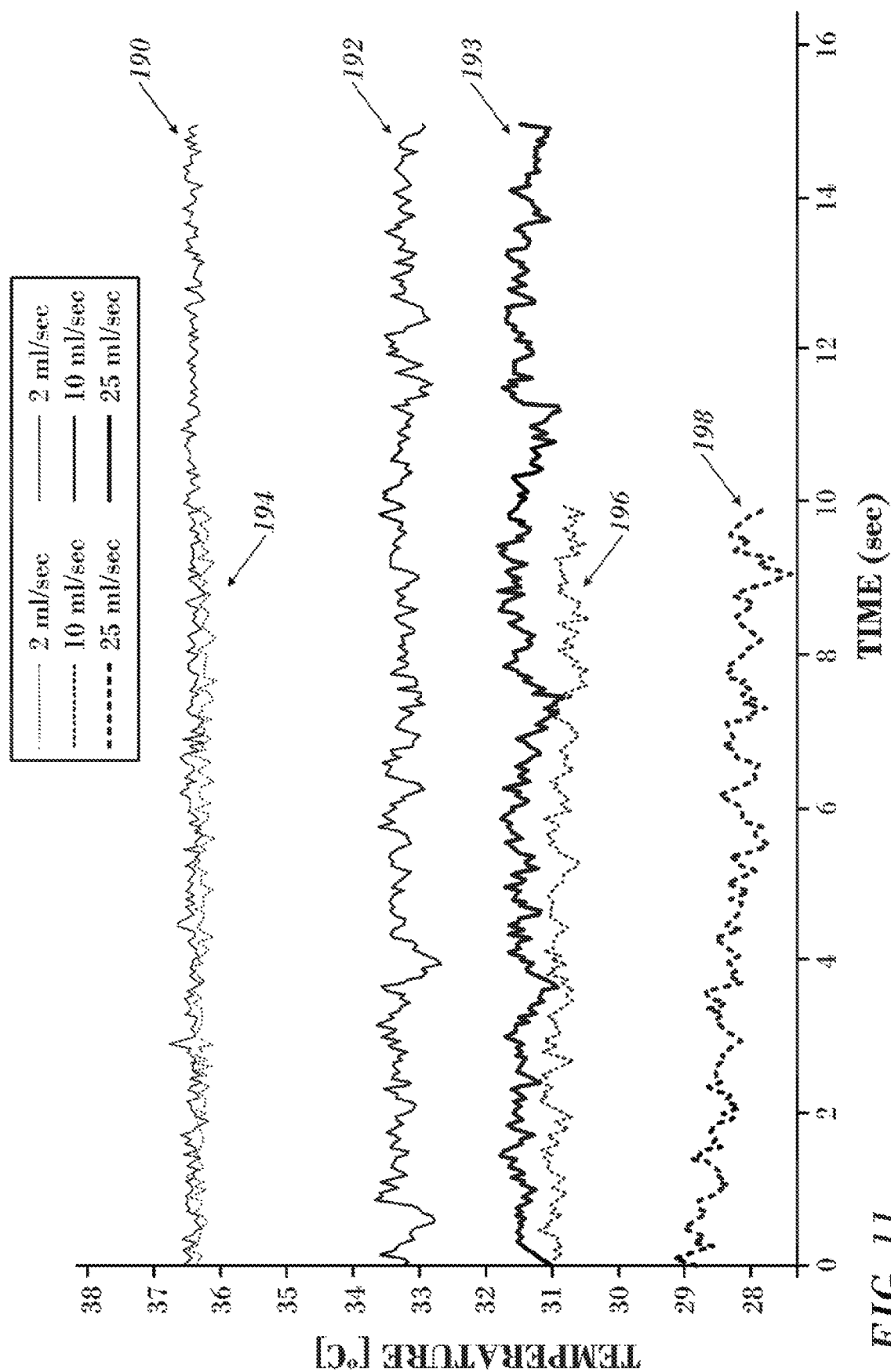
FIG. 11 is a composite display comparing the graphs shown in FIG. 9 and FIG. 10 in accordance with an embodiment of the invention.

Reference is now made to FIG. 11, which is a composite display comparing the graphs shown in FIG. 9 and FIG. 10 in accordance with an embodiment of the invention. At very low flow rate there is a minimal effect of flow rate variation. Tracings 190, 192 are nearly identical. At intermediate flow rates residual evidence of tissue cooling is seen. Thus, the temperature is almost the same in contact and non-contact conditions. However, the greater the flow the larger the temperature effect (i.e., the difference between the tracings 198, 193 (25 ml/sec) is larger than the difference between the tracings 196, 192.

Figure 12:
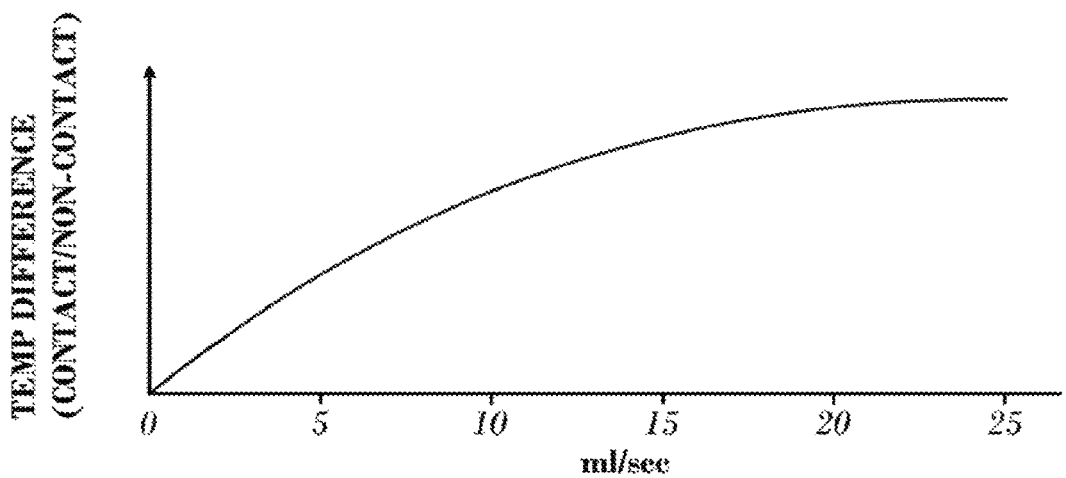
FIG. 12 is a plot showing the difference between temperatures during contact and non-contact between the catheter and tissue taken from the data in FIG. 11 in accordance with an embodiment of the invention.

Reference is now made to FIG. 12, which is a plot showing the difference between temperatures during contact and non-contact between the catheter and tissue taken from the data in FIG. 11 in accordance with an embodiment of the invention. A non-linear relationship is shown. The actual relationship may vary according to the characteristics of the catheter and the tissue being targeted; however a general non-linear increase in temperature difference and flow rate is expected to persist in most if not all cases.

Second Alternate Embodiment

Figure 13:
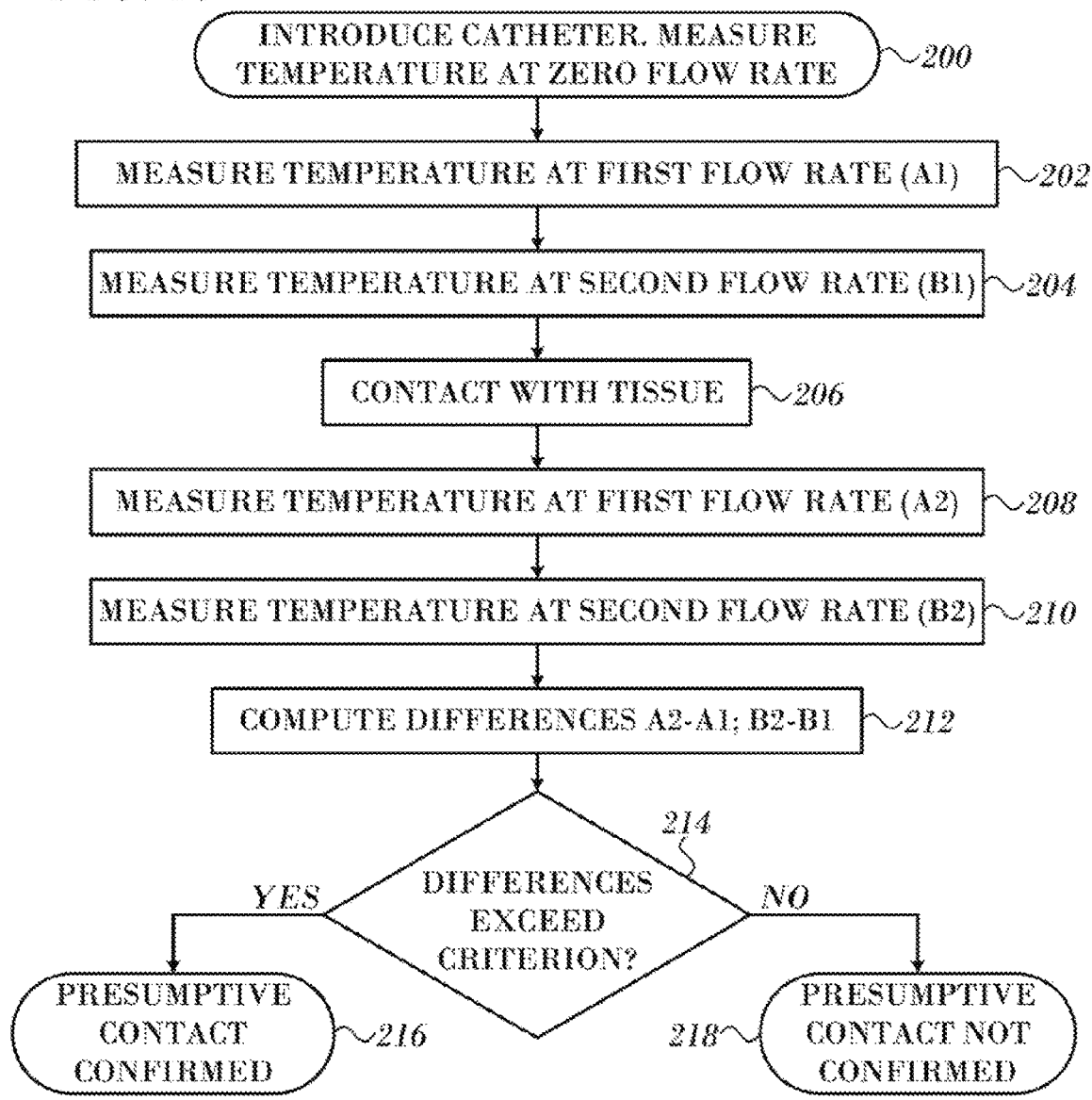
FIG. 13 is a flow chart of a method of determining contact between a catheter and a tissue in accordance with an alternate embodiment of the invention.

Reference is now made to FIG. 13, which is a flow chart of a method of determining contact between a catheter and a tissue in accordance with an alternate embodiment of the invention. The method should be understood with reference to Example 2 and FIG. 12.

The procedure begins with initial step 200. The catheter is introduced into the chamber in a non-contacting relationship with tissue. Blood temperature is determined as described above at zero flow rate. Temperature measurements are taken in this and subsequent steps of the method using one of the procedures described above in the discussion of FIG. 6.

Next, at step 202, while the catheter remains in a non-contacting relationship with tissue, irrigation fluid is passed at a first flow rate. This may be 10 ml/sec as described above, but other rates may be substituted.

Next, at step 204, while the catheter remains in a non-contacting relationship with tissue, irrigation fluid is passed at a second flow rate. This may be 25 ml/sec as described above, but other rates may be substituted.

Next, at step 206 the catheter is brought into presumptive contact with the target tissue, typically the wall of the cardiac chamber.

Next, at step 208, while the catheter remains in a presumptive contact with tissue, irrigation fluid is passed at the first flow rate as in step 202.

Next, at step 210, while the catheter remains in a presumptive contact with tissue, irrigation fluid is passed at the second flow rate as in step 204.

Next, at step 212 the respective temperature differences for the measurements during non-contact (and presumptive contact are computed for the first and second flow rates.

Next, at decision step 214, it is determined if the differences computed in step 212 are significant. This may be done by optimizing a figure of merit for a pro-file of the sort shown in FIG. 12, by employing the teachings, mutatis mutandis, of commonly assigned application Ser. No. 13/589,347, entitled Machine Learning in Determining Catheter Electrode Contact, which is herein incorporated by reference. Other techniques for such optimizations are well known in the art. Alternatively, when the differences exceed a threshold value for one or both of the differences computed in step 212 presumptive contact may be confirmed. The actual values for the threshold are application dependent, as noted above. Further alternatively, other characteristics of the temperature differences may be used as decisional criterion, for example the maximum value of $\Delta(temp)/\Delta(flow)$ in the plot of FIG. 12.

If the determination at decision step 214 is affirmative, then control proceeds to final step 216. Confirmation of presumptive contact between the catheter and the tissue is reported.

If the determination at decision step 214 is negative, then control proceeds to final step 218. Presumptive contact between the catheter and the tissue cannot be confirmed. Presumably the catheter tip is still free in the chamber.

This method of determining contact is particularly useful when conventional techniques of determining contact fail or are not available, for example when a fault in a contact force sensor or a malfunction in the mapping processor or circuitry occurs during a procedure. Moreover, the method described in Example 2 and FIG. 13 can be used to predict the temperature threshold in FIG. 8.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the steps of:
   introducing a probe into a fluid-filled body cavity of a subject, the fluid-filled body cavity having a temperature, the probe having a temperature sensor on a distal portion of the probe thereon, the body cavity having an interior wall;
   passing an irrigating fluid through the probe, wherein the irrigating fluid exits the probe at the distal portion into the body cavity, and wherein a temperature of the irrigating fluid is different from the temperature of the body cavity;
   while passing the irrigating fluid, recording temperature readings of the temperature sensor, wherein recording temperature readings comprises recording a first temperature reading and thereafter recording a second temperature reading, the contact criteria comprising the second temperature reading being lower than the first temperature reading, the method further comprising reporting a contact between the probe with the interior wall responsively to the determination and wherein the second temperature reading comprises transient elevations between 1 to 4 degrees C. that are between 0.3 to 5 seconds in duration and the method still further comprising reporting an intermittent contact between the probe and the interior wall;
   making a determination from the temperature readings that predetermined contact criteria between the probe and the interior wall of the body cavity are satisfied; and
   thereafter alerting an operator that the contact criteria are satisfied.

2. The method according to claim 1, wherein passing the irrigating fluid is performed multiple times at different flow rates.

3. The method according to claim 2, further comprising deriving a blood temperature and an irrigation fluid temperature from the temperature readings at the respective different flow rates of the irrigating fluid.

4. The method according to claim 1, wherein the contact criteria comprise criteria for stable contact between the probe and the interior wall of the body cavity.

5. The method according to claim 1, wherein the contact criteria comprise criteria for unstable contact between the probe and the interior wall of the body cavity.

6. The method according to claim 1, wherein the contact criteria comprise criteria for an absence of contact between the probe and the interior wall of the body cavity.

7. The method according to claim 1, wherein the temperature sensor comprises a plurality of temperature sensors, and recording temperature readings is performed concurrently with the temperature sensors.

8. The method according to claim 7, further comprising thermally insulating the temperature sensors from the irrigating fluid passing through the probe.

9. The method according to claim 7, wherein the temperature sensors are disposed on an external surface of the probe.

10. The method according to claim 7, wherein the temperature sensors are disposed internally in the probe.

11. The method according to claim 1, wherein the second temperature reading is at least 1° C. lower than the first temperature reading.

12. The method according to claim 1, wherein the second temperature reading is at least 4° C. lower than the first temperature reading.

13. The method according to claim 1, further comprising filtering the temperature readings to remove effects of heart rate variations and respiratory fluctuations.

14. The method according to claim 1, wherein the steps of passing an irrigating fluid and recording temperature readings comprise:
   while maintaining the probe in a non-contacting relationship with the interior wall of the body cavity recording first temperature readings at first and second flow rates;
   while maintaining the probe in a presumptively contacting relationship with the interior wall of the body cavity recording second temperature readings at first and second flow rates;
   computing respective differences between the first temperature readings and the second temperature readings at the first and second flow rates; and
   determining from the respective differences whether the distal portion of the probe is in contact with the interior wall.

* * * * *